(12) United States Patent
Lurie et al.

(10) Patent No.: US 7,207,951 B1
(45) Date of Patent: Apr. 24, 2007

(54) APPARATUS FOR OBTAINING BIOLOGICAL SAMPLES

(75) Inventors: Israel Raleigh Lurie, East Kew (AU); Donald Ian Phillips, Bayswater North (AU)

(73) Assignee: Diagnotech Pty. Ltd., Melbourne, Victoria (AU)

( * ) Notice: Subject to any disclaimer, the term of this patent is extended or adjusted under 35 U.S.C. 154(b) by 498 days.

(21) Appl. No.: 10/049,456

(22) PCT Filed: Aug. 11, 2000

(86) PCT No.: PCT/AU00/00962

§ 371 (c)(1),
(2), (4) Date: Aug. 21, 2002

(87) PCT Pub. No.: WO01/12072

PCT Pub. Date: Feb. 22, 2001

(30) Foreign Application Priority Data

Aug. 13, 1999 (AU) .................................. PQ2197

(51) Int. Cl.
*A61B 5/00* (2006.01)
*B65D 81/00* (2006.01)

(52) U.S. Cl. ............... 600/578; 600/563; 600/571

(58) Field of Classification Search ........... 600/562, 600/563, 570, 571, 573, 576, 578, 581; 604/192, 604/195, 196, 197, 198, 218
See application file for complete search history.

(56) References Cited

U.S. PATENT DOCUMENTS 3,626,928 A * 12/1971 Barringer et al. .......... 600/563
3,636,940 A    1/1972 Gravlee
4,088,135 A *  5/1978 O'Neill ................. 604/100.01
4,182,328 A *  1/1980 Bolduc et al. ............. 604/515
4,194,513 A    3/1980 Rhine et al.
4,265,249 A *  5/1981 Schindler et al. .......... 600/573
4,468,216 A *  8/1984 Muto ......................... 604/43
4,533,345 A *  8/1985 Louw ......................... 604/43
4,643,196 A    2/1987 Tanaka et al.
4,693,257 A    9/1987 Markham
4,744,789 A *  5/1988 Johnson ..................... 604/218
4,932,947 A *  6/1990 Cardwell .................... 604/198
5,007,903 A *  4/1991 Ellard ........................ 604/195

(Continued)

FOREIGN PATENT DOCUMENTS

FR    2 315 951 A    1/1977

*Primary Examiner*—Max F. Hindenburg
*Assistant Examiner*—Rene Towa
(74) *Attorney, Agent, or Firm*—Hogan & Hartson LLP

(57) ABSTRACT

A device for collection of a fluid sample, particularly a biological sample from an internal cavity of a mammal, comprises a barrel having an opening at one end thereof, a plunger operable axially within the barrel, the barrel and the plunger defining a fluid chamber having a volume which varies on axial movement of the plunger within the barrel, and a hollow, elongate tube extending from the fluid chamber through the opening in the barrel, the tube being in operative engagement with the plunger for axial movement to extend and retract the tube within respect to the barrel on axial movement of the plunger, and the tube being in fluid communication with the fluid chamber to provide a fluid flow path to and from the fluid chamber through the hollow tube. A method for collection of a fluid sample from an internal cavity of a mammal is also disclosed.

22 Claims, 3 Drawing Sheets

U.S. PATENT DOCUMENTS

| | | | |
|---|---|---|---|
| 5,217,023 A | | 6/1993 | Langdon |
| 5,238,003 A | * | 8/1993 | Baidwan et al. ............. 600/578 |
| 5,304,150 A | * | 4/1994 | Duplan et al. ............. 604/195 |
| 5,338,297 A | * | 8/1994 | Kocur et al. ............ 604/103.03 |
| 5,485,853 A | * | 1/1996 | Stubbs ........................ 600/565 |
| 5,494,044 A | * | 2/1996 | Sundberg .................... 600/562 |
| 5,624,399 A | * | 4/1997 | Ackerman ............. 604/103.03 |
| 5,738,109 A | * | 4/1998 | Parasher ...................... 600/569 |
| 5,836,921 A | * | 11/1998 | Mahurkar ................... 604/195 |
| 5,964,735 A | | 10/1999 | Alexander |
| 6,146,373 A | * | 11/2000 | Cragg et al. ................. 604/523 |

\* cited by examiner

APPARATUS FOR OBTAINING BIOLOGICAL SAMPLES

This is a National stage entry under 35 U.S.C. § 371 of Application No. PCT/AU00/00962 filed Aug. 11, 2000; the disclosure of which is incorporated herein by reference.

FIELD OF THE INVENTION

This invention relates to a device or apparatus for obtaining a biological sample from a human or other animal, and in particular it relates to a device or apparatus for obtaining a biological sample from an internal cavity, for example, an internal cavity of an organ such as the uterus. The biological sample may comprise a fluid, cells (such as endometrial cells) or cellular debris or other biological material, or both. In a preferred embodiment of the present invention, the device or apparatus is used to obtain fluid and cell samples from the human female reproductive system.

BACKGROUND OF THE INVENTION

There is a frequent need for medical and veterinary practitioners and other skilled personnel to collect biological samples from various internal cavities. Generally available devices for collecting samples comprise a syringe having a barrel with a flexible catheter attached to the end of the syringe barrel. The catheter must be carefully inserted into the internal cavity from which the sample is to be obtained, and then the plunger of the syringe depressed and withdrawn to collect the biological sample. Such a process is time consuming, requires the use of two hands by the person collecting the sample, and can lead to considerable discomfort for the patient. Frequently, the need for two hands to perform the process requires an assistant to be present, which will increase costs and has the potential to cause increased embarrassment and discomfort to a human patient.

Women aged between 45 and 60 years of age appear to be more susceptible than other age groups to cellular abnormalities of the reproductive system. As outlined above, the procedures currently employed to obtain samples may cause discomfort, inconvenience and are prolonged procedures which may be embarrassing for most women.

For many years the so-called "Pap" smear tests have been employed to detect abnormal cells in the cervix. However, to examine the internal lining of the uterine cavity, or endometrium, a more invasive diagnostic biopsy or curettage procedure is employed. The biopsy procedure may be carried out in a doctor's surgery, but curettage involves admitting the patient to hospital and the removal of tissue under anaesthetic. These procedures remove cells from the endometrium that are then forwarded to be assessed by a pathologist.

A new and simpler procedure for detection of endometrial cancer, which is described in International Patent Application No. PCT/AU98/00189 (WO 98/42865), tests for certain enzymes and other biological substances produced by the cells of the internal lining of the uterus. Samples are obtained by flushing the uterine cavity with saline solution and conducting tests on the wash-saline. The procedure does not require anaesthetics or admission to hospital and can be conducted in the surgery by a general practitioner.

Presently available sampling syringes with a flexible catheter as described above are, in general, unsuitable for carrying out this new procedure due to excessive leakage of the wash-saline during the procedure. Moreover, the wash-saline samples often contain blood and other contaminating cells that need to be removed by centrifuging the wash-saline to obtain a cell-free supernatant. In addition, the operator cannot be sure of the position of the catheter in the uterus or the efficiency of irrigation of the uterine cavity.

The device of the present invention enables a biological wash sample to be obtained from the internal cavity of an organ such as the uterus with minimum discomfort. A concomitant feature is that the device can be operated by a medical or veterinary practitioner (or other skilled person) without additional assistance. As a result, the device of the present invention permits the effective collection of a biological wash sample from an internal cavity in minimum time, with minimum interference to the patient and with maximum expectation that the collected sample will be suitable for its intended diagnostic or other application(s).

SUMMARY OF THE INVENTION

According to one aspect of the present invention, there is provided a device for collection of a fluid sample, comprising a barrel having an opening at one end thereof, a plunger operable axially within the barrel, said barrel and said plunger defining a fluid chamber having a volume which varies on axial movement of the plunger within the barrel, and a hollow, elongate tube extending from the fluid chamber through said opening in the barrel, said tube being in operative engagement with said plunger for axial movement to extend and retract the tube with respect to the barrel on axial movement of the plunger, and said tube being in fluid communication with the fluid chamber to provide a fluid flow path to and from the fluid chamber through the hollow tube.

Preferably, the device of the present invention is a syringe-like device having a generally cylindrical barrel and a plunger operable axially within the barrel. Preferably also, the hollow tube is a flexible, hollow catheter. A key feature of the device is the extendable/retractable hollow tube attached to the plunger and extending from the fluid chamber of the device through the opening at one end of the barrel to provide a fluid flow path to the fluid chamber through the hollow tube. More specifically, when the plunger is depressed so as to decrease the volume of the fluid chamber, fluid (for example saline or another wash fluid) will be forced from the fluid chamber through the hollow tube. Conversely, withdrawal of the plunger so as to increase the volume of the fluid chamber will aspirate fluid through the hollow tube and back into the fluid chamber. This movement of fluid provides the means for obtaining a biological sample from an internal cavity of a human or other animal such as the uterus of a human female by passing wash fluid through the tube and into the uterus and subsequently aspirating the wash fluid so as to collect a sample from the uterus in the fluid chamber of the device. Accordingly, in a further aspect of the present invention, there is provided a method for collection of a fluid sample from an internal cavity of a mammal, said method comprising the steps of:

(i) locating the end of a hollow tube at the opening of the internal cavity;

(ii) penetrating the internal cavity by moving the tube into the cavity while simultaneously passing wash fluid through the hollow tube to wash at least a portion of the surface of the internal cavity; and (iii) subsequently retracting the tube from the cavity while simultaneously collecting a fluid sample by aspirating the wash fluid through the hollow tube.

BRIEF DESCRIPTION OF THE DRAWINGS

One embodiment of a device in accordance with the present invention is shown by way of example only in the accompanying drawings, in which:

FIG. 3A shows the device in the "start" position, FIG. 3B in the "closed" position and FIG. 3C in the "open" position. Such a configuration permits total removal of the plunger and attached catheter (FIG. 3E) leaving the barrel which can be capped at either end as the storage vessel for the fluid wash sample (FIG. 3D).

DETAILED DESCRIPTION OF THE INVENTION

Figure 1A:
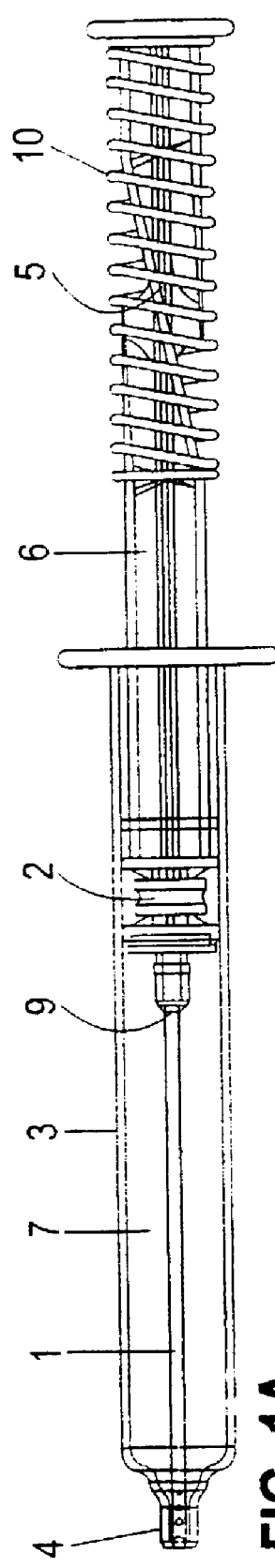
FIG. 1 is a sectional view along the axis of a device in accordance with the present invention showing the device in three different stages of use thereof.

Referring to the Figures, FIG. 1 is a diagrammatic representation of one embodiment of the device of the present invention. Such a device is suitable for obtaining a biological wash sample from an internal cavity of an animal or human. Without restriction to any particular usage, and for the purpose of illustration only, a device designed for collection of a uterine wash sample is described. As a result, the dimensions and the arrangement and number of perforations in the catheter have been selected for this purpose. It will be evident that different dimensions and arrangement of perforations may be preferred for other applications and all such variations and modifications fall within the overall ambit of the present invention.

Similarly, the filter system described in this embodiment is located attached to the plunger, however once again it will be evident that the filter system may be provided at other positions within the device.

The described arrangement is a preferred arrangement if testing of the wash sample is to be performed at a later stage or a separate location. Conversely, if testing of the wash sample is to occur with minimum delay, a simpler device without a filter may be preferred. In yet another embodiment, it may be desirable to subject the cells or cellular debris contained within the biological wash sample to some test procedure or examination. In this instance, the filter may be removed from the device after collection of the wash sample, and cells or cellular debris collected on the filter removed therefrom for testing or examination. Alternatively, a simple device without a filter may be preferred, with any contaminating cells or cellular debris being subsequently separated by filtration, centrifugation or other suitable process.

Turning now to FIG. 1, in this embodiment of the invention, a flexible, hollow, elongate catheter (1) is attached to a plunger (2) which is free to move axially within a barrel (3). The barrel has an opening at the end (4) through which the catheter can move as the plunger is depressed, i.e. moved axially into the barrel. The plunger has spiral mouldings (5) on the shaft (6) so that when the plunger is moved axially within the barrel, it will rotate within the barrel leading to a concomitant rotation of the catheter attached to it. A coil spring (10) is interposed between the plunger and barrel such that axial movement of the plunger when manual pressure is applied to it will result in compression of the coil spring, and removal of manual pressure on the plunger will result in reverse axial movement of the plunger as a direct action of potential energy within the coil spring.

The device may be supplied ready-to-use in which case a biologically acceptable wash solution will be provided in the fluid chamber (7) within the barrel. Alternatively, the device may be supplied empty, and the wash solution loaded into the chamber (7) as required.

The hollow catheter (1) has perforations (8) at or near its remote end, that is the end remote from the plunger. The number, size and exact location of these perforations will vary depending upon the particular application. In a preferred arrangement for a device designed for collection of a uterine wash sample, the tip of the catheter is sealed, two perforations approximately 4 mm from the tip are made at 0° and 180° and two smaller perforations approximately 8 mm from the tip are made at 90° and 270°. Such an arrangement allows good irrigation of the whole uterine cavity and minimises the risk of damage to cells lining the cavity. It will be appreciated that the above example is one of many possible arrangements, all of which fall within the broad scope of the present invention.

Figure 2A:
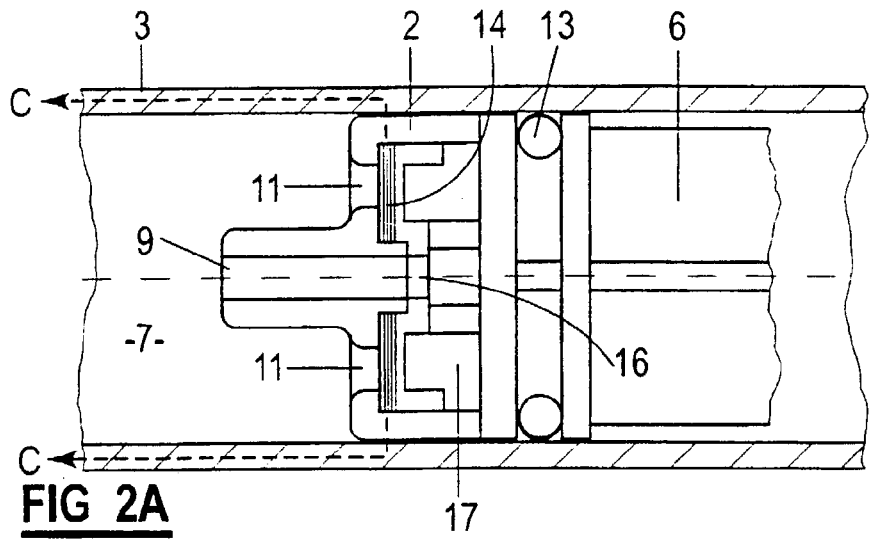
FIGS. 2A and 2B are sectional views along the axis of the device in the area of the plunger showing first and second embodiments of the optional filter system in the plungers.
Figure 2B:
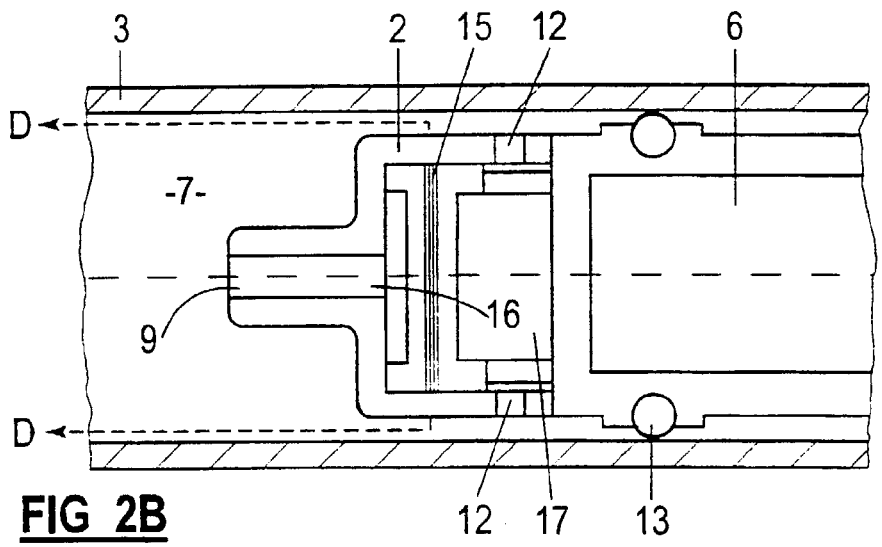
Figure 2C:
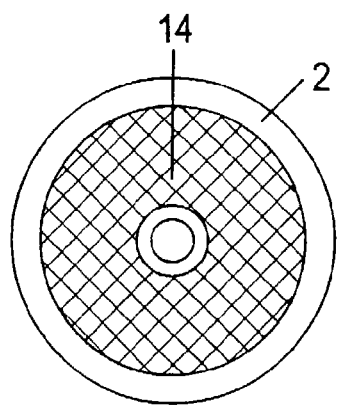
FIGS. 2C and 2D are cross-sectional views taken on the lines C—C and D—D of FIGS. 2A and 2B respectively showing the filter surface of the first and second embodiments of the filter system in the plunger.
Figure 2D:
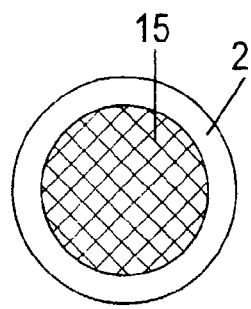
Figure 3A:
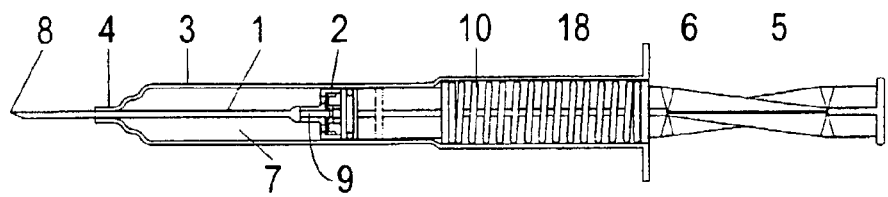
FIGS. 3A to C are sectional views along the axis of the device showing a modified configuration in which the return spring is contained within an extension of the barrel.
Figure 3B:
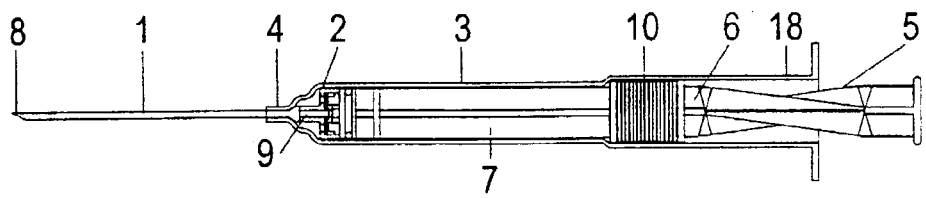
Figure 3C:
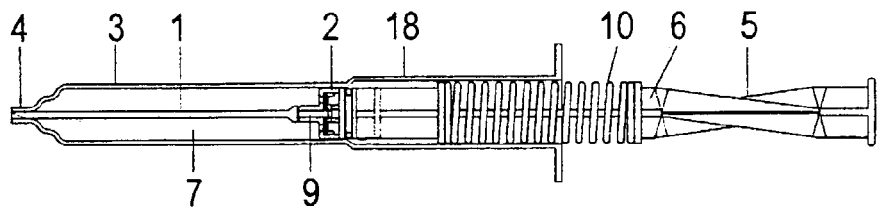
Figure 3D:
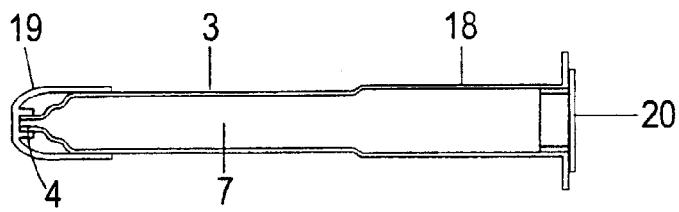
Figure 3E:
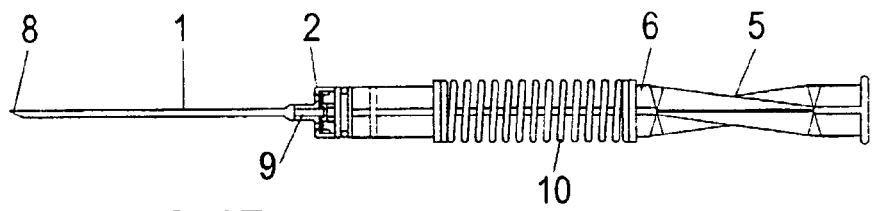

Use of the device of the invention requires that the wash solution in the fluid chamber (7) be able to enter the hollow catheter (1) and then exit through perforations (8). In one embodiment of the invention, the end (9) of the cathether near the plunger (2) may be sealed by attachments to the plunger, and perforations are provided at or near this end. In an alternative embodiment, shown in FIG. 2, the catheter is fixed within the plunger with its end (9) open into a chamber (17) in the plunger as shown (2), with the chamber (17) being in fluid communication with the fluid chamber (7) through the apertures (11 or 12). As the plunger (2) is moved axially within the barrel (3) to reduce the volume of fluid chamber (7), wash solution passed through apertures in the plunger end (FIGS. 2A, 11) or side (FIGS. 2B, 12) which are proximal to the plunger seal (13) and then enters the catheter through the open end (16). An annular (FIGS. 2A and 2C, 14) or circular (FIGS. 2B and 2D, 15) filter may be positioned in the line of the fluid path between fluid chamber (7) and the hollow catheter (1).

In the modified configuration of the device shown in FIG. 3, coil spring (10) is located within an extension (18) of the barrel (3). The other components of this embodiment are as described above with reference to FIG. 1, and optional caps (19, 20) are shown in FIG. 3D so that the barrel (3) can be used as a storage vessel for the collected wash sample.

In a further embodiment, the device of the present invention may be fitted with brushes or other cell-collecting structures to permit the collection of endo and/or ecto-cervical cells simultaneously with collection of a uterine wash sample. Thus, a cell brush or similar structure may be fitted over the flexible catheter (1) and located at or adjacent to the end (4) of the barrel of the device so that the catheter can move freely through it. The brush may have an outer part consisting of radial and/or axially projecting hairs.

Before use, a biologically suitable wash solution is introduced into the barrel. Phosphate buffered saline, pH 7.2 (PBS) is a typical, though non-limiting example of such a solution. In one embodiment, the hollow catheter has perforations at or near its end attached to the plunger to permit passage of fluid between the barrel and the catheter. In an alternative embodiment, fluid can pass from the barrel via a chamber formed in the plunger into the catheter at the end of the catheter attached to the plunger. In either embodiment, the catheter also has perforations at or near its remote end to permit passage of fluid between the catheter and the internal cavity from which the biological sample is to be obtained. Variations in the nature, number and exact position of these perforations may be made to optimise the device for a given application. Specific variations suitable for collection of a wash sample from a human female are described above. However, it should be obvious to one of ordinary skill in this field that the size and nature of the internal cavity will influence this design.

The above described basic device can either be used alone or in conjunction with one or more of a number of accessory design components. Such accessory design components are illustrated by, but in no way limited to the following. Other variations, modifications and additions will be developed to adapt the basic device to specific applications. However such variations, modifications and additions, whilst utilising the basic design functionality of the above described device, remain simple modifications within the scope of the present invention.

i. Filter to Substantially Remove Contaminating Cells and Debris.

Samples from internal cavities often contain blood and other cells that can render the sample unsuitable for testing. This is particularly true if testing cannot be undertaken shortly after sample collection. The cells and debris can be removed after collection by passing the collected wash specimen through a suitable filter into a final container. Alternatively, as described in the detailed description above, a filter arrangement can be incorporated within the basic device. The filter may be within the catheter, within the plunger, or within the barrel. It is only required that the design cause the wash fluid, after collection, to pass through the filter before entering the final collection vessel. In certain circumstances it may be desirable to separate the filtered wash fluid from the filters. Such circumstances are well-known to those skilled in the art. A configuration of the device of the invention which will permit such separation is shown in FIG. 3.

ii Return Spring, Pneumatic Cushion or Other Return Device.

To facilitate the single-handed operation of the basic device, a coil spring, pneumatic cushion or other return device, can be fitted between the barrel of the device and the plunger so that, once the plunger is depressed thereby delivering the wash fluid to the internal cavity, release of pressure on the plunger will result in the gradual withdrawal of the wash sample from the internal cavity back to the barrel. Withdrawal of wash fluid should preferably take 5 to 30 seconds; more preferably 10 to 25 seconds. To achieve this preferred rate of withdrawal, the coil spring, pneumatic cushion or other return device should be carefully matched to the dimensions of the basic device. As an alternative, the coil spring, pneumatic cushion or other return device may be more powerful than required, the return therefore being guided by a gentle release of pressure on the plunger by the operator.

iii Simultaneous Collection of Cell Samples.

In certain circumstances, e.g. collection of a uterine wash sample, it may be useful to also collect cell samples for histological examination for abnormal cell appearance. Both ecto- and endo-cervical cell samples can be simultaneously collected by attachment of a brush or similar device as described above. A soft cervical plug can also be used proximal to the brush to cap this attachment to prevent uterine washings reaching and contaminating the brush.

iv Graduated Plunger Rod.

To permit ready estimation of the distance of penetration of the catheter into the internal cavity, the plunger shaft may be provided with readily recognisable graduations to indicate the distance of movement of the plunger and therefore of the catheter.

v Spiral Moulding in Plunger.

In a further embodiment of the device, the plunger shaft may be provided with a spiral twist such that the plunger will rotate during depression. Preferably, during a full depression, the plunger will rotate between 90 and 360°, more preferably between 120 and 270°, and most preferably between 150 and 210°. This plunger rotation will result in a concomitant rotation of the catheter, thus improving the efficiency of irrigation of the internal cavity from which the biological wash sample is being collected.

vi Small Protrusions in Catheter Tip.

In a further specialised embodiment, cells collected within the uterine wash sample can be useful for diagnostic testing. To ensure a suitable quantity of cells are present in the wash, the catheter of the device may be provided with very small protrusions at or adjacent to its tip. Such protrusions will have a mild abrasive action on the uterine lining at the catheter is introduced and withdrawn thus increasing the cellular content of the uterine wash sample.

The use of a preferred embodiment of the present invention will now be described in the following non-limiting Examples.

EXAMPLE 1

Figure 1B:
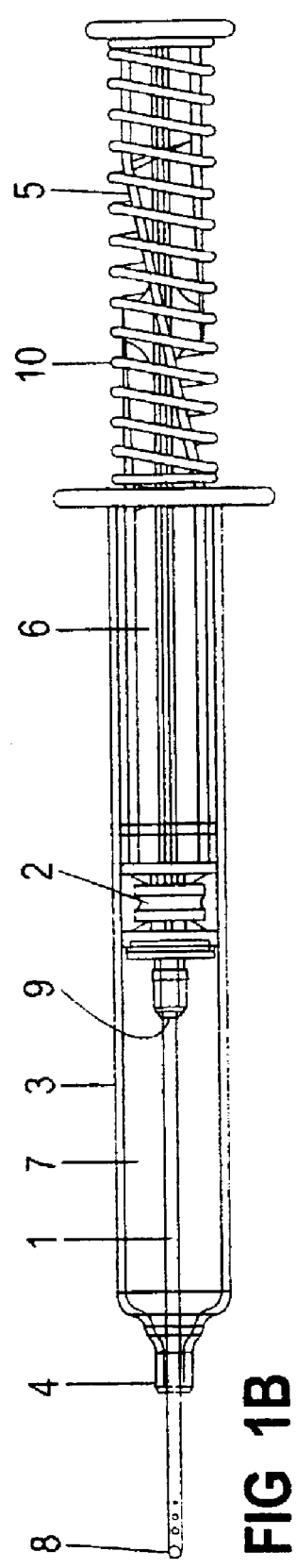
Figure 1C:
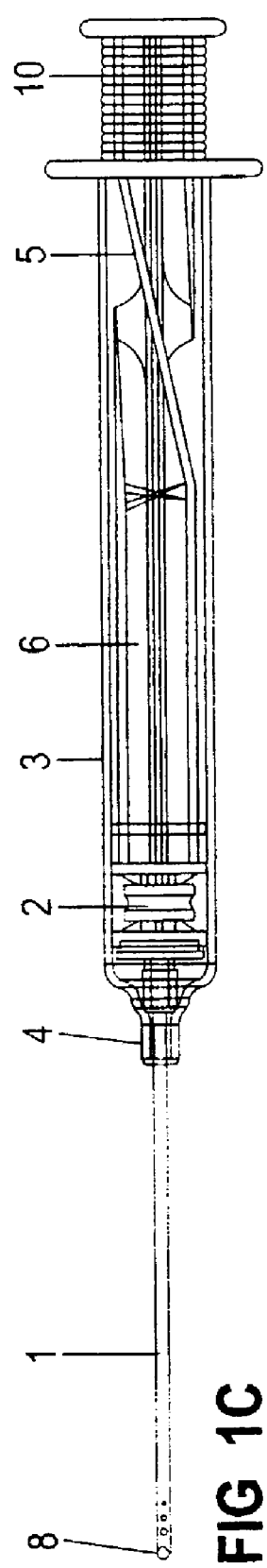

Collection of Uterine Wash Sample Using Device Supplied Empty and not Fitted with Cervical Brushes or Filters The device was removed from its protective bag and the plunger (2) manually depressed thus causing the catheter (1) to extend from the barrel (3) (FIG. 1B). The protruding catheter end was inserted in a container of saline, then the plunger fully depressed to the "closed" position (FIG. 1C), thereby dispelling air from the fluid chamber (7). Relaxation of pressure upon the plunger (2) causes the coil spring (10) to withdraw the plunger thereby initiating flow of saline through perforations (8) into the catheter and thence from the open end (16) of the catheter into the fluid chamber (7). The plunger is withdrawn to the "open" position (FIG. 1A), and then with the device in a vertical position, with the plunger end of the barrel uppermost, the plunger was depressed to the "start" position (FIG. 1B) to expel air from the fluid chamber (7) and expose the remote end of catheter (1) ready for insertion into the cervix.

The apparatus was then ready for the uterine irrigation and draining procedure. To conduct the procedure, the vagina was held open with a speculum and the apparatus positioned in the vagina with the short protruding length of the catheter (1) inserted into the cervix. The plunger was gently depressed, causing the end of the catheter to move into the uterus and at the same time to spray the endometrial lining of the uterus with saline via perforations (8). Spiral mouldings (5) on the plunger shaft (6) cause twisting of the catheter (1) thus further increasing the efficiency of irrigation through the perforations (8). This process was continued until the whole length of the uterus had been irrigated, when the catheter (1) was extended in the manner shown in FIG. 1C.

Markings on the plunger shaft (6) indicate the depth of insertion of the catheter in the uterus. The maximum length of the catheter, as measured from the cervical entrance, is about 7 cm. If the uterine cavity is shorter than this then the flexible catheter will bend and so not damage the lining. Usually the operator will notice that resistance to forward motion has increased, indicating that the catheter (1) has reached the top of the uterus.

With the apparatus still firmly plugging the cervix, the plunger was slowly drawn back to the "start" position (FIG. 1B), assisted by the spring (10), withdrawing the catheter (1) and at the same time aspirating the uterine wash saline into the catheter (1) via perforations (8). The wash sample passed up the hollow catheter to its end (16) where it passed into the fluid chamber (7).

The wash sample was then either subjected to diagnostic assessment with minimal delay, or passed through a filter to substantially remove cells and cell debris.

EXAMPLE 2

Collection of Uterine Wash Sample Using Device Supplied Empty and Fitted with Cervical Brushes and Filter All procedures were the same as described in Example 1 until the plunger was withdrawn to the "start" position (FIG. 1B) after having collected the biological wash sample. Prior to removal of the device, the barrel of the device was gently rotated by a twisting action thereby rubbing the brush located at the end (4) of the barrel in and against the cervix to obtain the ecto- and endo-cervical cell samples.

EXAMPLE 3

Collection of a Uterine Wash Sample with a Ready-to-Use Device

The procedure was the same as described for Examples 1 and 2, except that the device was supplied already filled with saline in the fluid chamber (7), and the device in the "open" position shown in FIG. 1A. Preferably, in such a ready-to-use device, the end (4) of the barrel is sealed with a removable cap.

What is claimed is:

1. A device for collection of a fluid sample, comprising a barrel having an opening at one end thereof, a plunger operable axially within the barrel, said barrel and said plunger defining a fluid chamber having a volume which varies on axial movement of the plunger within the barrel, and a flexible, hollow, elongate catheter extending from the fluid chamber through said opening in the barrel, said catheter being sufficiently flexible so as to be adapted to bend and follow the conformation of an internal cavity upon encountering walls of said cavity during insertion into said cavity without damaging tissue of said cavity, said catheter further being in operative engagement with said plunger for axial movement to extend and retract the catheter within respect to the barrel on axial movement of the plunger, and said catheter being in fluid communication with the fluid chamber so as to provide fluid flow to and from the fluid chamber through the catheter during extending and retracting, respectively, of the catheter.

2. A device according to claim 1, wherein said catheter extends into a chamber in the plunger which is in fluid communication with said fluid chamber.

3. A device according to claim 1, wherein one end of said catheter is attached to said plunger and said catheter is provided with perforations in the wall thereof at or near the end thereof attached to the plunger for fluid communication with said fluid chamber.

4. A device according to claim 1, wherein one end of said catheter is attached to said plunger and the end of said catheter remote from the plunger is sealed, and the catheter is provided with perforations in the wall thereof at or near the sealed end for passage of fluid in and out of the hollow catheter.

5. A device according to claim 1, further comprising a filter located in the fluid flow path to and from the fluid chamber through the hollow catheter.

6. A device according to claim 5, wherein the filter is adapted to substantially remove cells and cellular debris from a fluid in said fluid flow path.

7. A device according to claim 5, wherein the filter is located in the hollow catheter.

8. A device according to claim 5, wherein the filter is located in the plunger.

9. A device according to claim 5, wherein the filter is located in the barrel.

10. A device according to claim 1, further comprising a return device located between the barrel and the plunger of the device.

11. A device according to claim 1, further comprising means for rotating the plunger on axial movement of the plunger within the barrel of the device.

12. A device according to claim 11, wherein said means for rotating is adapted to rotate the plunger from 90° to 360° on full axial movement of the plunger within the barrel.

13. A device according to claim 1, further comprising means for collecting a sample of cells or cellular debris, said means being located on said barrel at or adjacent to said opening at one end thereof.

14. A device according to claim 13 wherein said means for collecting a sample of cells or cellular debris comprises a brush or brush-like device.

15. A method for collection of a fluid sample from an internal cavity of a mammal, said method comprising:
   (i) locating a distal end of a flexible, hollow, elongate catheter at an opening of the internal cavity;
   (ii) penetrating into the internal cavity by moving the catheter into the cavity while simultaneously passing wash fluid through the hollow catheter to wash at least a portion of the surface of the internal cavity during said penetrating; and
   (iii) subsequently retracting the catheter from the cavity while simultaneously collecting a fluid sample by aspirating the wash fluid through the hollow catheter during said retracting.

16. A method according to claim 15, wherein the mammal is a human.

17. A method according to claim 16, wherein the internal cavity is the uterus of a human female, and the fluid sample is a uterine wash sample.

18. A method according to claim 15, comprising the further step of filtering the fluid sample to substantially remove cells and cellular debris from the fluid sample.

19. A method according to claim 15, wherein a sample of cells or cellular debris is simultaneously collected at the opening of the internal cavity.

20. A method according to claim 19, wherein the sample is a sample of at least one of ectocervical or endocervical cells.

21. A method for collection of a fluid sample from an internal cavity of a mammal utilizing a fluid collection device, said method comprising:
(i) providing a fluid collection device comprising a barrel having an opening at one end thereof, a plunger operable axially within the barrel, said barrel and said plunger defining a fluid chamber having a volume which varies on axial movement of the plunger within the barrel, and a flexible, hollow, elongate catheter extending from the fluid chamber through said opening in the barrel, said catheter being in operative engagement with said plunger for axial movement to extend and retract the catheter within respect to the barrel on axial movement of the plunger, and said catheter being in fluid communication with the fluid chamber to provide a fluid flow path to and from the fluid chamber through the hollow catheter;
(ii) locating a distal end of said catheter at the opening of the internal cavity;
(iii) moving said plunger to cause said catheter to penetrate the internal cavity while simultaneously passing wash fluid from said fluid chamber out through the hollow catheter to wash at least a portion of the surface of the internal cavity during said penetrating; and
(iv) subsequently moving said plunger to cause said catheter to retract from the cavity while simultaneously collecting a fluid sample by aspirating the wash fluid through the hollow catheter during said retracting.

22. A device according to claim 10, wherein the return device is a coil spring located between the barrel and the plunger of the device.

* * * * *